United States Patent
Persson

(10) Patent No.: US 10,052,447 B2
(45) Date of Patent: Aug. 21, 2018

(54) COVERING SHEET

(75) Inventor: Jan-Ove Persson, Hoor (SE)

(73) Assignee: Atos Medical AB (SE)

( * ) Notice: Subject to any disclaimer, the term of this patent is extended or adjusted under 35 U.S.C. 154(b) by 594 days.

(21) Appl. No.: 14/123,419

(22) PCT Filed: May 31, 2012

(86) PCT No.: PCT/EP2012/060199
§ 371 (c)(1),
(2), (4) Date: Apr. 4, 2014

(87) PCT Pub. No.: WO2012/163994
PCT Pub. Date: Dec. 6, 2012

(65) Prior Publication Data
US 2014/0216445 A1  Aug. 7, 2014

(30) Foreign Application Priority Data

May 31, 2011 (SE) ........................ 1150506

(51) Int. Cl.
A61M 16/00 (2006.01)
A61M 16/04 (2006.01)
A61M 16/10 (2006.01)

(52) U.S. Cl.
CPC ...... *A61M 16/047* (2013.01); *A61M 16/0465* (2013.01); *A61M 16/0468* (2013.01); *A61M 16/1045* (2013.01)

(58) Field of Classification Search
CPC ................. A61M 16/00; A61M 16/04; A61M 16/0465–16/0472; A61M 16/06;
(Continued)

(56) References Cited

U.S. PATENT DOCUMENTS 4,867,146 A * 9/1989 Krupnick .................. A61F 9/00
128/858
4,890,608 A * 1/1990 Steer ....................... A61F 5/443
602/52
(Continued)

FOREIGN PATENT DOCUMENTS

EP  0507459 A1  10/1992
JP  H02-168947 A  6/1990
(Continued)

OTHER PUBLICATIONS

English abstract for JP-H09-156645.
(Continued)

*Primary Examiner* — Gregory Anderson
*Assistant Examiner* — Ned T Heffner
(74) *Attorney, Agent, or Firm* — Fishman Stewart PLLC

(57) ABSTRACT

A covering sheet for covering a skin adhesive surface of a device for holding a tracheostoma device over a tracheostoma of a patient may include a central/medial element for covering the central/medial part of the skin adhesive surface of the device. The covering sheet may include first and second elements arranged laterally of the central/medial element. Lateral peripheral borders of the central/medial element may be positioned adjacent medial peripheral borders of the first and second elements. The peripheral borders may be defined by division lines.

20 Claims, 3 Drawing Sheets

(58) Field of Classification Search
CPC ...... A61M 16/0666–16/0688; A61M 16/1045; A61M 25/00; A61M 25/0017; A61M 25/002; A61M 25/02; A61M 2025/0191; A61M 2025/0206–2025/0293; A61M 27/00; A61M 31/00; A61F 5/44; A61F 5/4401–5/449; A61F 2005/4402–2005/4495; A61F 13/82; A61L 24/00; Y10T 156/10
See application file for complete search history.

(56) References Cited

U.S. PATENT DOCUMENTS

| | | | |
|---|---|---|---|
| 5,088,483 | A | 2/1992 | Heinecke |
| 5,738,095 | A * | 4/1998 | Persson ................ A61F 2/20 128/201.13 |
| 6,830,565 | B2 | 12/2004 | Cisko, Jr. |
| 2010/0217215 | A1* | 8/2010 | Lykke ................ A61F 5/443 604/344 |
| 2010/0331785 | A1* | 12/2010 | Fabo ................ A61M 16/047 604/180 |

FOREIGN PATENT DOCUMENTS

| | | |
|---|---|---|
| JP | H09-156645 A | 6/1997 |
| WO | WO-99/61240 A1 | 12/1999 |
| WO | WO-2010070087 A2 | 6/2010 |

OTHER PUBLICATIONS

English abstract for JP-H02-168947.
English translation of Japanese Office Action for JP-2014-513183, dated Jan. 19, 2016.

* cited by examiner

COVERING SHEET

CROSS-REFERENCE TO RELATED APPLICATIONS

This application is a US National Phase of PCT/EP2012/060199, filed on May 31, 2012, which claims priority to SE 1150506-2, filed on May 31, 2011, both of which are hereby incorporated by reference in their entirety.

TECHNICAL FIELD

This invention pertains in general to a covering sheet for covering a skin adhesive surface of devices for holding a trachestoma device and a method for applying such a device. More particular the invention pertains to a multi parted covering sheet, for such application.

BACKGROUND

A tracheostomy is a surgical procedure in which an opening is formed through the anterior surface of the neck into the trachea. The opening is referred to as a tracheostoma. A tracheostomy tube can be provided to extend between the tracheostoma and the trachea. A tracheostomy is performed for example when there is a malfunction, such as a result from injury or disorder, in respect of the nervous system or the respiratory passages, which malfunction results in an incapacity to obtain enough air. An inferior lung capacity or need of respiratory treatment may also result in a tracheostomy.

A laryngectomy is a surgical procedure, used for example to treat a carcinoma, which involves removal of the larynx or voice box and the creation of a tracheostoma. A consequence of the procedure is that the trachea is no longer connected to the pharynx but is diverted to the tracheostoma. After this procedure, normal nasal function is not possible. In a subject whose breathing functions normally, the nose and the mucous membrane lining of the nasal cavity perform important functions in conditioning inhaled air. The convoluted passages and rich blood supply serve to increase both the temperature and humidity of the inhaled air to minimise the differential in these parameters with those of the surface of the lungs. Normally some heat and moisture is also captured from exhaled air prior to its release to the atmosphere. The mucous lining of the nasal passages also serves to remove particulate matter, such as fine dust particles, pollutants and microorganisms, from the inhaled air, and the action of cilia transports mucous and any particles away from the lungs.

When a patient has received a laryngectomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air flow, can be closed to divert the airflow.

In this respect tracheostoma devices, such as filter devices, HME, breathing protectors, and speech valves, have been developed to enable moisturizing of inhaled air, removal of small particles and bacteriological substances in said inhaled air, and providing the patient with the ability to speech by closing the air passage through the trachestoma by manual operation.

These tracheostoma devices are held in place by a tracheostoma device holder, arranged above the tracheostoma of the patient. The tracheostoma device holder is attached to the skin of the patient by a plaster, having an adhesive surface on the side of the plaster intended to be directed towards the patient in use. Either, the tracheostoma device holder is welded to the plaster, or the tracheostoma device holder is on an adhesive surface on the side of the plaster intended to be directed outwards from the patient in use. On the skin adhesive surface a covering sheet may be applied, which is removed just before application of the tracheostoma device holder. The covering sheet facilitates transportation, and maintains skin adhesive ability of the skin adhesive surface.

SUMMARY

It is however a problem associated with the application of the tracheostoma device holder after the removal of the covering sheet, since the throat of the patient receiving the tracheostoma device holder by no means is planar. I is difficult to adhere the tracheostoma device holder in the pit in between the sternocleidomastoid muscles, at patients with sunken stomas, i.e. stomas that somewhat has sunken into the throat of the patient, since the adhesive surface of the tracheostoma device holder inevitably will adhere to the walls of the pit before reaching the bottom of the pit with the central portion of the system. Sunken stomas are very frequent in the group of patients not having the two vertical sternocleidomastoid muscles on the neck cut during laryngectomy. As a result, it is very common that the tracheostoma device holder flip over, since the bad connection between adhesives and skin and the axial displacement of the speech pressure resulting in loosening of the tracheostoma device holder and need of unduly high speech pressure. Furthermore, since the tracheostoma device holder systems according to the prior art expose the entire adhesive surface on the side intended to face the patient, before application, application is difficult due to high demands of exact and correct initial positioning of the tracheostoma device holder system is required. Otherwise, the tracheostoma device holder has to be disengaged and repositioned, resulting in decreased skin adhesive property and risk of leakage with every repositioning.

Furthermore, in many hospitals the surgical steps during laryngectomy are adapted for creating stomas of substantially planar natures, to comply with the tracheostoma device holder system presently on the market. This adaptation includes the cutting of the two vertical sternocleidomastoid muscles on the neck.

In an attempt to overcome these problems with the prior art WO 2010/070087 discloses a multi parted covering sheet, which may be removed from the skin adhesive surface of the tracheostoma device holder in sequence, such that parts of the skin adhesive surface of the tracheostoma device holder are revealed and attached to the skin in sequence. The covering sheet arrangement herein is however unnecessarily thick, due to folded lateral covering sheets. Also, due the folded lateral covering sheets, there tends to be a string of uncovered skin adhesive surface in between the lateral covering sheet elements and the central covering sheet, since the central covering sheet continues over the lateral covering sheet elements.

Hence, an improved covering sheet arrangement for a tracheostoma device holder would be advantageous, and in particular a covering sheet arrangement allowing for convenient application of the system with improved positioning ability, maintained skin adhesive property over the entire skin adhesive surface of the tracheostoma device holder, and decreased thickness of the covering sheet arrangement, etc.

Accordingly, the present invention preferably seeks to mitigate, alleviate or eliminate one or more of the above-identified deficiencies in the art and disadvantages singly or in any combination and solves at least the above mentioned problems by providing a covering sheet for covering the skin adhesive surface of a device for holding a tracheostoma device over a tracheostoma of a patient, said covering sheet comprising: a central/medial element for covering the central/medial part of the skin adhesive surface of a device; first and second elements being arranged laterally of the central/medial element, wherein the peripheral border of the central/medial element is positioned adjacent medial peripheral borders of the first and second elements, said peripheral borders being defined by division lines; a device for holding a tracheostoma device, comprising a passage, giving the device a distal and a proximal opening, for receiving the tracheostoma device in/at the distal opening thereof; a flange, extending laterally, caudially, and cranially from the through passage, said flange having a proximal side, intended to face the tracheostoma of the patient, and a distal side, intended to face outwardly from the patient, at least a part of said proximal side being skin adhesive, wherein a covering sheet (200) according to above is arranged on said proximal side; and a method for applying a device according to above over a stoma of a patient, comprising the steps of: removing at least the medial/central element; positioning the device over the stoma of the patient; adhering the skin adhesive proximal side of the flange of the device to the skin of the neck covered by at least the medial/central element; removing the first and second elements; and adhering the skin adhesive proximal side of the flange of the device to the skin of the neck covered by the first and second elements.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a covering sheet for application on the skin adhesive surface of a system for holding a tracheostoma device over a tracheostoma of a patient.

Figure 1:
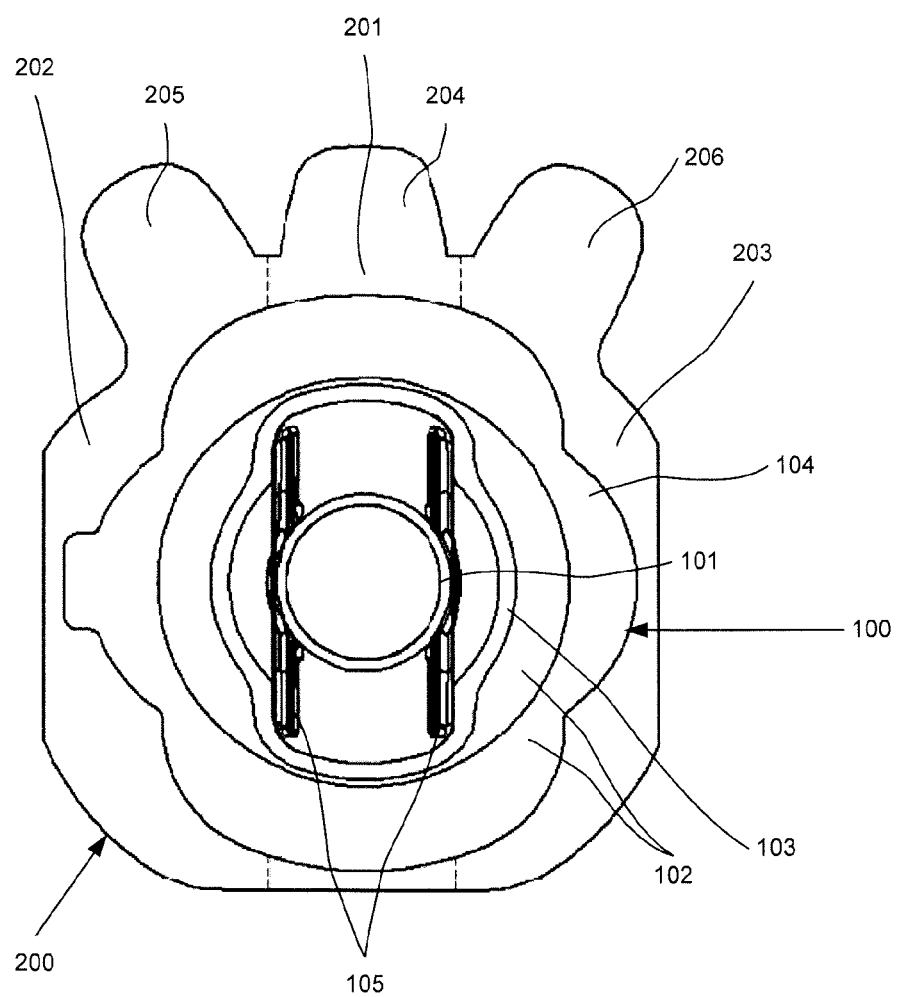
FIG. 1 is frontside view of a tracheostoma device holder, with a covering sheet according to one embodiment of the present invention arranged on the backside.
Figure 2:
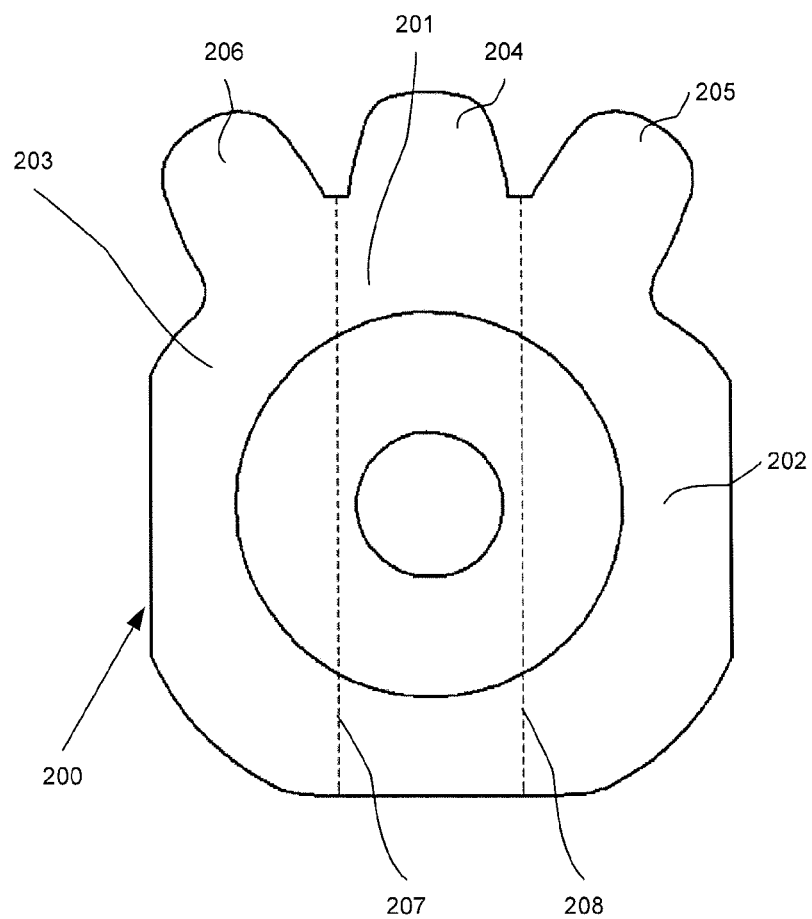
FIG. 2 is backside view of a tracheostoma device holder, with a covering sheet according to one embodiment of the present invention arranged on the backside.

According to a first embodiment, disclosed in a frontside view in FIG. 1, a system for holding a tracheostoma device over a tracheostoma of a patient, i.e. a tracheostoma device holder, 100 is disclosed. A corresponding backside view is disclosed in FIG. 2. A tracheostoma device may in this context be a HME, speech valve, etc. The device comprises a tubular portion for receiving the tracheostoma device in the distal end thereof. The tubular portion may be of a circular cross-section, in a plane perpendicular to the central axis of the tubular portion. In the proximal end of the tubular portion 101 a flange 102 is provided, around the proximal opening of the tubular portion 101. The flange 102 comprises an inner rigid portion 103 and an outer more flexible portion 104. The flange 102 extends radially outwards from a proximal part of the tubular portion 101, in a plane perpendicular to the central axis of the tubular portion 101, said plane being the dorsal plane in use. The flange 102 has a proximal side, intended to face the tracheostoma of the patient, and a distal side, intended to face outwardly from the patient.

The flange 102 is inclined, distally towards the central axis of the tubular portion 101, at least in the inner rigid portion 103. Preferably, the entire rigid portion 103 is inclined distally towards the central axis of the tubular portion 101, whereby improved contact with sunken stomas may be achieved.

The distal side of the flange 102 is provided with reinforcement. The reinforcement extends centrally in the caudal/cranial direction, giving a higher moment of resistance in the caudal/cranial direction than in the lateral/medial direction for the device 100. The higher moment of resistance in the caudal/cranial direction may be obtained by having a higher moment of resistance in the caudal/cranial direction than in the lateral/medial direction for at least a part of said flange 102. The reinforcement will absorb the speech pressure and transfer the obtained force centrally in the caudal/cranial direction. In this direction, there is more room for connection area between the device and the patient than in the lateral/medial direction, whereby flipping over may be prevented, while making the dimension in the lateral/medial direction smaller, allowing for improved accessibility with the entire depth of sunken stomas. The result will be improved resistance against flipping over, and better connection between the device and the stoma, leading to reduced risk of loosening of the device, evidently leading to undue leakage. The reinforcement may be a bracing means 105. Even if the bracing means 105 could be localized on the proximal side of the flange 102, it is preferred to have the bracings 105 on the distal side, since such location would make possible a smooth and even contact surface between the device 100 and the skin of the patient. Also, it is convenient to have the bracings 105 on the distal side, since the inclination of the flange 102 allows for a concavely shaped distal side, whereby the bracings 105 may be placed confidently low, i.e. sufficiently far to the proximal end, to make possible a satisfactory stiffness, while simultaneously not being prone to interaction with clothing etc.

The bracing means 105 are preferably ribs extending in a plane perpendicular to the central axis of the tubular portion 101, thus being the dorsal plane in use. In this connection the ribs extend in the caudal/cranial direction. However, the bracing means 105 may also be a higher material thickness in the caudal/cranial direction than in the lateral/medial direction.

In one embodiment, two ribs extend substantially tangentially with the circular tubular portion 101 and parallel with each other, such that they in use extend along the caudal/ cranial extension of the neck of the patient. In this way the device 100 may have a heterogeneous plasticity, whereby the device 100 has a higher deformation resistance in the direction parallel with the extension of the bracing means 105, i.e. the caudal/cranial direction, than in the direction perpendicular to the extension of the bracing means 105, i.e. the medial direction. Thus, the flange 102 of the device 100 may be compressed medially, i.e. in a direction perpendicular to the caudal/cranial direction, while keeping the shape of the tubular portion 101, thereby assuring that the positioning of the tubular portion 101 over the stoma and in between the two sternocleidomastoid muscles is achieved. Thus, no cutting of the two sternocleidomastoid muscles is necessary when using the device according to the present invention. Due to the convexly shaped proximal side of the flange 102, the device may come in good skin contact also on sunken stomas.

Along and adjacent the bracing means 105 in the caudal/cranial direction the device is provided with two weakening lines, to further increase the difference in moment of resistance between the caudal/cranial direction and the lateral/medial direction for said device 100. In this way the weakening lines give rise to reinforcement in the caudal/cranial direction.

The proximal side of the flange 102 is skin-adhesive. In one embodiment only parts of the proximal side is skin-adhesive. The skin-adhesive part may extend all the way from the periphery of the device to the tubular portion 101. In this connection the skin adhesive part may be the proximal side of a flexible sheet onto which the more rigid inner part 103 is welded. Thereby, the outer part of the flexible sheet, skin-adhesive on the proximal side, will be the flexible part 104 of the flange 102. Preferably, the weld is located radially distanced from the tubular portion 101, such as at the periphery of the more rigid part 103. In this way, the skin-adhesive part may be adhered to the skin at higher stress conditions in the distal direction, since the weld will take up the stress on a distance away from the edge of the skin adhesive part.

The inner rigid portion 103 of the flange 102 is preferably oval, having its approximated longest diameter in the same direction as the extension direction of the bracing means 105, i.e. in the caudal/cranial direction of a caudal/cranial axis. Similarly, the approximated smallest diameter is in the lateral/medial direction of a lateral/medial axis. Also the outer more flexible portion 104 may be substantially circular or oval with indentations, such that for example a flower shape is obtained. In this way it may be easier to adhere the outer parts of the flange to the skin of the patient, without the need of folding the flexible portion to compensate for irregularities in the shape of the neck of the patient. In this way the contact area between the device 100 and the skin of the patient may be kept sufficiently high, within the two sternocleidomastoid muscles, to allow for safe attachment of the device to the skin of patients with sunken stomas.

On the proximal side of the device 100 a covering sheet 200 may be arranged, for facilitating transportation, storing, and application of the device 100. In FIG. 1 the covering sheet is illustrated from a front side view, thus arranged behind/proximally of the tracheostoma device holder. The covering sheet may for example be of a suitable polymer, such as a thermoplastic polymer. Suitable thermoplastic polymers are polyethylene and polypropylene. In one embodiment the covering sheet 200 is made of polypropylene. The covering sheet 200 surrounds the proximal opening of the device 100. The covering sheet 200 comprises a central/medial element 201, and a first and a second side element 202, 203, arranged laterally of the central element 201. The first and the second side elements 202, 203 are applied from the tubular element 102 laterally on each side of the tubular element 102, respectively, covering side segments of the adhesive surface of the device 100. Thus, the central/medial segment of the adhesive surface of the device 100 will still be uncovered by the first and the second side elements 202, 203, once the central/medial element 201 has been removed from the skin adhesive surface of the device 100. The central/medial segment of the adhesive surface of the device 100 will be the surface that in use will extend upwards and downwards from the tubular element 102 in a caudal/cranial direction, said central/medial segment being adapted in size and form to fit within the two sternocleidomastoid muscles. The central/medial element 201 and the first and second side elements may each be provided with a tab, 204, 205, 206, respectively, to facilitate removal of the elements. The tabs 204, 205, 206 may extend outside the periphery of the skin adhesive surface of the device 100, to further facilitate removal of the elements 201, 202, 203, respectively.

The central/medial element 201 and the first and second elements 202, 203 are arranged in one layer/sheet, such that the lateral peripheral border of the central/medial element 201 is arranged adjacent and in close contact with the medial peripheral border of the first and second elements 202, 203. Simultaneously, the central/medial element 201 forms the periphery of the covering sheet 200, at least partly. In one embodiment the periphery of the central/medial element 201 forms the periphery of the covering sheet 200 at the central/medial part at the cranial end and/or the caudal end. When the periphery of the central/medial element 201 forms the periphery of the covering sheet 200 at the central/medial part at the cranial end and the caudal end, the first and second elements 202, 203 are entirely separated by the central/medial element 201, such that they not are in close contact. In this way a vertical division of the covering sheet 200 into a medial/central element 201, a first lateral element 202, and a second lateral element 203 has been obtained. It is preferred to keep the distance between the central/medial element 201 and the first and second elements 202, 203 as small as possible. This may be accomplished by razor blade cutting division lines 207, 208, to divide the covering sheet 200 into said central/medial element 201 and said first and second elements 202, 203.

In one embodiment the covering sheet 200 is made of a mono-oriented thermoplastic polymer, such as a mono-oriented polypropylene (MOPP). Mono-oriented polymer means that the polymer material has polymer molecules substantially oriented in one direction. The orientation of the mono-oriented polymer may then coincide with the caudal/cranial direction of the intended use, such that the division lines 207, 208 substantially coincide with the direction of the mono-orientation of the mono-oriented polymer. When a cut, such as a cut by razor blade or razor blade cutter, is performed, there is no need to cut entirely through the covering sheet, while still obtaining satisfactory separation of the elements when removing for example the medial/central element 201. Thus, division lines 207, 208 are in the form of trenches in the covering sheet 200, i.e. wherein also the bottom of the cuts of the division lines are comprised in the covering sheet 200. Thus, the first and second elements 202, 203 may remain in place after the removal of said central/medial element 201, without entirely separating the elements through cutting. The pulling of the element to be removed will initiate full rupture of the division lines, without being accompanied by the other elements. Also, a too deep cut of the covering sheet 200 when forming the division lines will decrease the strength of the covering sheet 200.

It is also possible to form the division lines 207, 208 as perforation lines.

Figure 3:
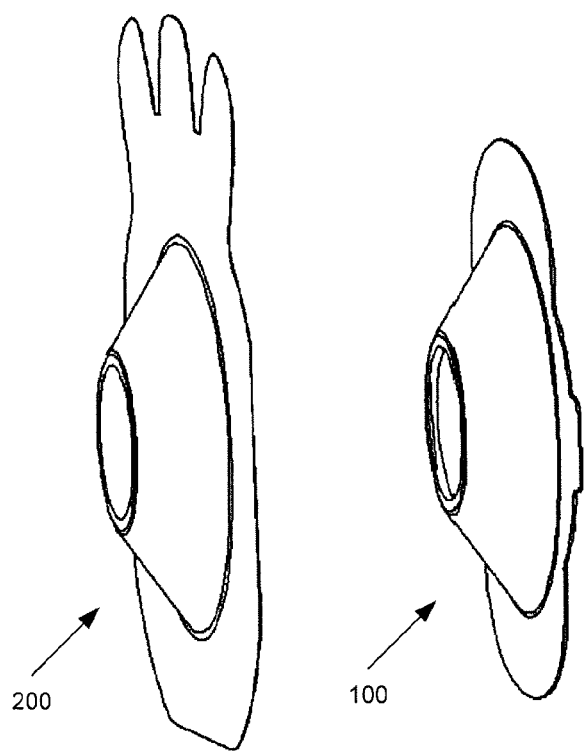
FIG. 3 is an isometric view of a trachestoma device holder, with a covering sheet according to one embodiment of the present invention arranged on the backside.

When applying the covering sheet 200 on a device 100 with convex proximal surface, in accordance with above and FIG. 3, it is highly preferable to keep the elements 201, 202, 203 (not shown in FIG. 3) connected. Otherwise, the elements will be pushed further apart during application, since the convex shape will urge such separation. In such circumstances it is highly preferable to have the division lines 207, 208 in form of perforation lines or trenches, since then the elements 201, 202, 203 will conform to the convex proximal side of the device 100 without being separated from each other. In one embodiment the division lines 207, 208 in form of perforation lines or trenches may comprise an edge cut extending entirely through the covering sheet 200, to facilitate initialization of division along said division lines 207, 208. Such edge cut may then have an extension of 1 mm to 10 mm, such as 2 to 7 mm.

To improve the covering ability of the covering sheet 200 the covering sheet 200 is heat shaped together with the device 100, to obtain the three-dimensional convex shape at the proximal surface of the device 100. Thus, it is preferred to manufacture the covering sheet 200 a polymer with low melting point, such as polyethylene or polypropylene, preferably covered by a silicone coating for improved separation between the adhesive surface and the covering sheet.

In this way, a user or applier may (i) position the device 100 over the stoma of the patient, after the central/medial covering element 201 of the covering sheet 200 has been removed, by holding on the first and second elements 202, 203; squeezing the device 100 in the medially direction, without deforming the tubular part 102 too much, due to the bracing means 105, and safely apply the device with good skin contact, even on sunken stomas, due to the convexly shaped proximal side of the flange 102, whereby the application of the device 100 is facilitated by only having the central/medial segment of the device 100 skin-adhesive during application; thereafter (ii) pull the tabs 205, 206 laterally and thus removing the first and second elements 202, 203 and uncovering, in a lateral direction, the skin-adhesive parts there beneath, until the first and second elements 202, 203 have been removed and detached from the device 100, whereby the entire skin adhesive proximal side of the device 100 is exposed, and then (iii) press the flange 102 towards the patient to assure satisfactory adhesion between the flange 102 and the skin of the patient.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

The invention claimed is:

1. A device for holding a tracheostoma device, comprising:
   a passage for receiving the tracheostoma device;
   a flange extending from the through passage and having a proximal side with a skin adhesive; and
   a covering sheet is arranged on said proximal side of the flange, the covering sheet including:
      a central/medial element that at least partly forms an outer periphery of the covering sheet, and
      first and second elements arranged laterally of the central/medial element,
      wherein peripheral borders of the central/medial element are positioned adjacent to and along medial peripheral borders of the first and second elements, said peripheral borders being defined by division lines extending in a caudal/cranial direction, thereby dividing the covering sheet from one single-layer sheet into at least three elements including the central/medial element and the first and second elements.

2. The device according to claim 1, wherein the central/medial element is provided with a through hole for correspondence with a proximal opening of the device.

3. The device according to claim 1, wherein the peripheral borders of the central/medial element are arranged adjacent to a medial peripheral border of the first and second elements, respectively.

4. The device according to claim 1, wherein the central/medial element at least in part forms at least a portion of a periphery of the covering sheet.

5. The device according to claim 1, wherein the outer periphery of the central/medial element forms at least a portion of a periphery of the covering sheet.

6. The device according to claim 1, wherein the division lines only partly penetrate the covering sheet.

7. The device according to claim 1, wherein the division lines are perforation lines.

8. The device according to claim 1, wherein at least one of the central/medial element and the first and second elements are provided with a tab to facilitate removal of the respective first and second elements.

9. The device according to claim 8, wherein the tab is configured to extend outside the outer periphery.

10. The device according to claim 1, wherein the covering sheet is made of a mono-oriented polymer.

11. The device according to claim 10, wherein the direction of the division lines at least partly coincides with an orientation of the mono-oriented polymer.

12. The device according to claim 1, wherein the covering sheet is made of a thermoplastic polymer.

13. The device according to claim 12, wherein the thermoplastic polymer is at least one of polyethylene or polypropylene.

14. A device for holding a tracheostoma device, comprising:
   a passage, giving the device a distal and a proximal opening, for receiving the tracheostoma device in/at the distal opening thereof; and
   a flange, extending laterally, caudally, and cranially from the passage, said flange having a proximal side, intended to face the tracheostoma of the patient, and a distal side, configured to face outwardly from the patient, at least a part of said proximal side being skin adhesive, wherein a covering sheet is arranged on said proximal side, the covering sheet including:
a central/medial element for covering a central/medial part of a skin adhesive surface of the proximal side, the central/medial element including a through hole for correspondence with the proximal opening, wherein said central/medial element at least partly forms an outer periphery of the covering sheet;
first and second elements being arranged laterally of the central/medial element, wherein
peripheral borders of the central/medial element are positioned adjacent and attached along medial peripheral borders of the first and second elements, said peripheral borders being defined by division lines extending in a caudal/cranial direction, thereby dividing the covering sheet from one single-layer sheet into at least three elements including the central/medial element and the first and second elements.

15. The device according to claim 14, wherein the device includes a tubular portion for holding a speech valve.

16. The device according to claim 14, wherein the proximal side includes a convexly shaped part.

17. The device according to claim 14, wherein at least one of the central/medial element and the first and second elements are provided with a tab to facilitate removal of the elements.

18. The device according to claim 14, wherein the division lines extend between an upper edge and a lower edge of the flange, and are formed by cutting the cover sheet into the at least three elements.

19. The device according to claim 14, wherein the division lines only partly penetrate the covering sheet.

20. The device according to claim 14, wherein the division lines include perforation lines.

* * * * *